(12) United States Patent
Fleury et al.

(10) Patent No.: US 12,364,465 B2
(45) Date of Patent: Jul. 22, 2025

(54) SYSTEMS AND METHODS FOR ECCENTRIC NODULE TISSUE ACQUISITION

(71) Applicant: Boston Scientific Scimed, Inc., Maple Grove, MN (US)

(72) Inventors: Sean Fleury, Princeton, MA (US);
Gary Leanna, Holden, MA (US);
Douglas Garrity, Waltham, MA (US);
Thinh Nguyen, Medford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 75 days.

(21) Appl. No.: 17/361,989

(22) Filed: Jun. 29, 2021

(65) Prior Publication Data

US 2021/0321994 A1    Oct. 21, 2021

Related U.S. Application Data

(63) Continuation of application No. 15/833,389, filed on Dec. 6, 2017, now Pat. No. 11,096,678.

(60) Provisional application No. 62/431,006, filed on Dec. 7, 2016.

(51) Int. Cl.
| | | |
|---|---|---|
| *A61B 10/04* | (2006.01) | |
| *A61B 1/00* | (2006.01) | |
| *A61B 1/018* | (2006.01) | |
| *A61B 8/00* | (2006.01) | |
| *A61B 8/08* | (2006.01) | |
| *A61B 8/12* | (2006.01) | |
| *A61B 10/02* | (2006.01) | |

(Continued)

(52) U.S. Cl.
CPC ............ *A61B 10/04* (2013.01); *A61B 8/0841* (2013.01); *A61B 8/12* (2013.01); *A61B 8/483* (2013.01); *A61B 10/0275* (2013.01); *A61B 10/0283* (2013.01); *A61B 1/00098* (2013.01); *A61B 1/018* (2013.01); *A61B 8/085* (2013.01); *A61B 2010/0208* (2013.01); *A61B 2017/3413* (2013.01); *A61B 2090/378* (2016.02)

(58) Field of Classification Search
CPC ......... A61B 10/04; A61B 8/0841; A61B 8/12; A61B 8/483; A61B 2017/3413
See application file for complete search history.

(56) References Cited

U.S. PATENT DOCUMENTS

| | | | |
|---|---|---|---|
| 2003/0013971 A1* | 1/2003 | Makin | A61B 8/4488 |
| | | | 600/459 |
| 2004/0034369 A1 | 2/2004 | Sauer et al. | |
| 2008/0058586 A1 | 3/2008 | Karpiel et al. | |

(Continued)

FOREIGN PATENT DOCUMENTS

| | | |
|---|---|---|
| JP | 2001104315 A | 4/2001 |
| JP | 4363719 B2 | 11/2009 |
| WO | 2015153931 A1 | 10/2015 |

*Primary Examiner* — Amal Aly Farag
(74) *Attorney, Agent, or Firm* — Seager, Tufte & Wickhem, LLP (57) ABSTRACT

The present disclosure relates to the field of endoscopy. Specifically, the present disclosure relates to systems and methods for real-time visualization and sampling of target tissue within body passages. In particular, the present disclosure relates to a system that provides real-time visualization of eccentric pulmonary nodules, and which allows the location/orientation of a biopsy needle to be determined prior to its first actuation.

10 Claims, 10 Drawing Sheets

(51) Int. Cl.
*A61B 17/34* (2006.01)
*A61B 90/00* (2016.01)

(56) References Cited

U.S. PATENT DOCUMENTS

| | | |
|---|---|---|
| 2010/0113878 A1 | 5/2010 | Kawano et al. |
| 2011/0152610 A1 | 6/2011 | Trusty et al. |
| 2011/0152616 A1 | 6/2011 | Deal et al. |
| 2013/0110089 A1* | 5/2013 | Kappel .................. A61B 1/018 606/1 |
| 2014/0005706 A1* | 1/2014 | Gelfand ................ A61N 7/022 606/169 |
| 2014/0276051 A1* | 9/2014 | Hoffman ............ A61B 17/3417 604/164.09 |
| 2014/0350401 A1* | 11/2014 | Sinelnikov ......... A61B 18/1492 606/169 |
| 2015/0073299 A1* | 3/2015 | Vetter ................ A61B 10/0266 600/564 |
| 2015/0335317 A1* | 11/2015 | Ellingson ........... A61B 10/0275 600/431 |
| 2015/0335859 A1* | 11/2015 | Klocke .................... A61F 2/82 604/103.1 |
| 2016/0192860 A1* | 7/2016 | Allenby ................ A61B 10/04 600/431 |
| 2016/0287223 A1* | 10/2016 | Hingston ................. A61B 8/12 |
| 2016/0367231 A1* | 12/2016 | Uemichi ............. A61B 1/0051 |

\* cited by examiner

SYSTEMS AND METHODS FOR ECCENTRIC NODULE TISSUE ACQUISITION

CROSS REFERENCE TO RELATED APPLICATIONS

This application is a continuation of Ser. No. 15/833,389, filed Dec. 6, 2017, which claims the benefit of priority under 35 U.S.C. § 119 to U.S. Provisional Patent Application Ser. No. 62/431,006, filed on Dec. 7, 2016, which is incorporated by reference in its entirety for all purposes.

FIELD

The present disclosure relates to the field of endoscopy. Specifically, the present disclosure relates to systems and methods for real-time visualization and sampling of target tissue within body passages.

BACKGROUND

Radial endobronchial ultrasound (R-EBUS) provides a minimally invasive option when clinical presentation indicates that tissue biopsy within the pulmonary passages is necessary. Conventional R-EBUS transbronchial needle aspiration (TBNA) involves delivering a radial ultrasound probe to the target airway through the working channel of a bronchoscope, visualizing the target pulmonary nodule on R-EBUS, locking placement of an access sheath, removing the radial ultrasound probe from the access sheath and then blindly advancing a biopsy needle to acquire cellular matter for cytologic evaluation. This blind sampling may often result in the biopsy needle completely missing the target nodule. To ensure that the target nodule is successfully biopsied, the medical professional typically actuates the biopsy needle into the pulmonary tissue multiple times while rotating the endoscope. Such repetitive biopsy needle actuations may result in a variety of negative medical outcomes, e.g., unnecessary trauma to healthy tissues surrounding the target nodule, reduced bleeding, increased likelihood of false-negative results, and increased procedure duration and cost. The inability to consistently and predictably acquire biopsy samples is especially problematic for eccentric (e.g., offset) pulmonary nodules, which occur in approximately 40% of all pulmonary procedures. Sampling of eccentric pulmonary nodules requires that either the catheter or biopsy needle is able to bend or flex within the narrow pulmonary passages.

Accordingly, various advantages may be realized by a system that provides real-time visualization of eccentric pulmonary nodules, and which allows the location/orientation of a biopsy needle to be determined prior to its first actuation.

SUMMARY

The present disclosure, in its various aspects, provides advantages in the medical field, such as the field of pulmonary endoscopy, of a sampling system that allows real-time visualization of eccentric pulmonary nodules, and which allows the location/orientation of a biopsy needle to be determined prior to its first actuation. In various embodiments, an offset biopsy needle and radial ultrasound transducer are disclosed, which may allow for accurate and efficient biopsy of eccentric pulmonary nodule tissue.

In one aspect, the present disclosure relates to an endcap, comprising a proximal end; a distal end; a first lumen extending between the proximal and distal ends to define a first opening; and a second lumen extending between the proximal end and an outer surface of the endcap to define a second opening. The first and second lumens may be separated by a variable thickness inner wall. A thickness of the inner wall may taper down from the distal end to the proximal end to define a ramped surface within the second lumen. The ramped surface may include an angle of approximately 5 degrees to approximately 10 degrees relative to a longitudinal axis of the endcap. The first lumen may be configured to receive an ultrasound transducer. The second lumen may be configured to receive a tissue sampling element. The endcap may include a variety of materials, including, but not limited to metallic or ceramic materials.

In another aspect, the present disclosure relates to a system, comprising a delivery device that includes first and second working channels; and an endcap comprising first and second lumens defining respective first and second openings. A proximal end of the endcap may be attached to a distal end of the delivery device such that the first working channel is contiguous with the first lumen, and the second working channel is contiguous with the second lumen. The first and second lumens may be separated by a variable thickness inner wall, in which a thickness of the inner wall may taper down from the distal end to the proximal end to define a ramped surface within the second lumen. The system may further include an ultrasound transducer disposed within the first working channel and first lumen. The ultrasound transducer may extend distally beyond the distal end of the endcap. The system may further include a tissue sampling element slidably disposed within the second working channel and second lumen. The proximal end of the endcap may be attached to a distal end of the delivery device by a heat shrink sleeve disposed about an outer surface of a proximal portion of the endcap and an outer surface of a distal portion of the delivery device. A distal portion of the delivery device may include a pocket that the endcap is configured to fit within. The pocket may include a skived opening configured to align with the second opening. The ultrasound transducer may be disposed within a sheath, wherein a portion of the sheath includes a radiopaque material. The radiopaque material may include, for example, a strip of radiopaque material which extends along a length of the sheath. A portion of the sheath may extends distally beyond the ultrasound transducer. The strip of radiopaque material and the second opening in the outer surface of the endcap may be offset by approximately 180 degrees.

In another aspect, the present disclosure relates to a method, comprising advancing a tissue sampling system through a body passage, wherein the tissue sampling system includes a delivery device comprising first and second working channels, and an endcap comprising first and second lumens defining respective first and second openings, wherein a proximal end of the endcap is attached to a distal end of the delivery device such that the first working channel is contiguous with the first lumen, and the second working channel is contiguous with the second lumen; imaging a target tissue with the body passage; advancing the tissue sampling element distally beyond the second opening of the endcap into the target tissue such that a portion of the target tissue is captured within a lumen of the tissue sampling element; and withdrawing the system from the body passage. The target tissue may be imaged under ultrasound using the ultrasound transducer. The tissue sampling element may be advanced into the target tissue simultaneous with the imaging of the target tissue.

BRIEF DESCRIPTION OF THE DRAWINGS

Non-limiting examples of the present disclosure are described with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to real-time visualization and sampling of eccentric pulmonary nodules, the systems and methods disclosed herein may be used to obtain biopsy samples from within a variety of body lumens, including, for example, the heart, vascular system, circulatory system, gastrointestinal (GI) tract, stomach, esophagus, urogenital system and the like. In various embodiments, the catheter endcap may be suitable for use with variety of tissue sampling tools (e.g., grasping or cutting elements) in addition to biopsy needles.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from a medical professional when introducing a device into a patient, while the term "proximal" refers to the end closest to the medical professional when introducing a device into a patient.

The present disclosure generally provides a dual-lumen catheter endcap which supports the side-by-side and simultaneous use of a tissue sampling element and a radial ultrasound transducer. The sloped or angled configuration of one of the lumens may provide the ability to sample eccentric nodules without requiring the tissue sampling element to include a pre-formed curvature. The dual-lumen endcap is compatible for use with a radial ultrasound transducer configured to provide real-time visualization of the target pulmonary nodule while simultaneously indicating the location/orientation of the biopsy needle relative to the radial ultrasound transducer prior to its first actuation. The dual-lumen cap and radial ultrasound transducer may also provide real-time visualization of the target pulmonary nodule and location/orientation of the biopsy needle for subsequent actuations into the same (or different) nodule.

Figure 1:
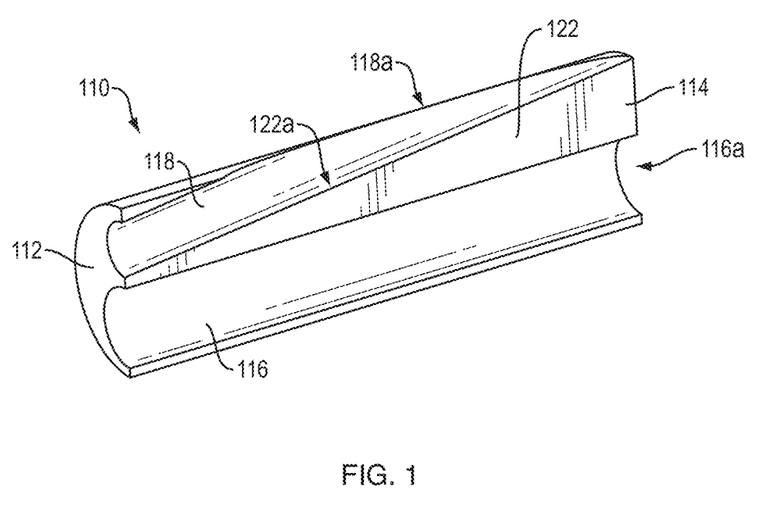
FIG. 1 provides a cross-sectional view of a catheter endcap, according to one embodiment of the present disclosure.

Referring to FIG. 1, in one embodiment, the present disclosure provides a catheter endcap 110 comprising a proximal end 112, a distal end 114 and first and second lumens 116, 118 separated by a variable thickness inner wall 122. The first lumen 116 may extend between the proximal and distal ends 112, 114 to define a first opening 116a. The second lumen 118 may extend between the proximal end 112 and an outer surface of the endcap 110 to define a second opening 118a. The first and second openings 116a, 118a are not limited to substantially circular and oblong shapes, respectively, but may include a variety of other shapes and/or configurations. The variable thickness inner wall 122 may taper down from the distal end 114 to the proximal end 112 such that the second lumen 118 defines a ramped surface 122a (e.g., sloped, angled, etc.). The ramped surface 122a may include an angle of approximately 5 degrees to approximately 10 degrees relative to a longitudinal axis (Li) of the endcap 110, and may include any degree of angle therebetween. The endcap may be unitarily formed from a variety of metallic, ceramic or hardened plastic materials, as are known in the art.

Figure 2A:
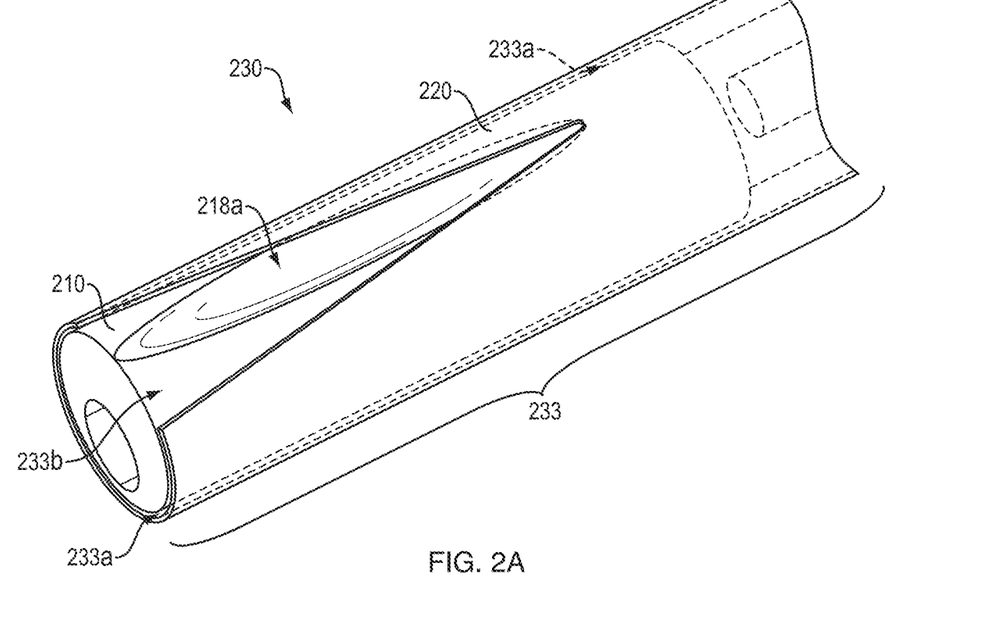
FIGS. 2A-2B provide schematic views of the catheter endcap of FIG. 1 attached to the distal end of a catheter, according to one embodiment of the present disclosure.
Figure 2B:
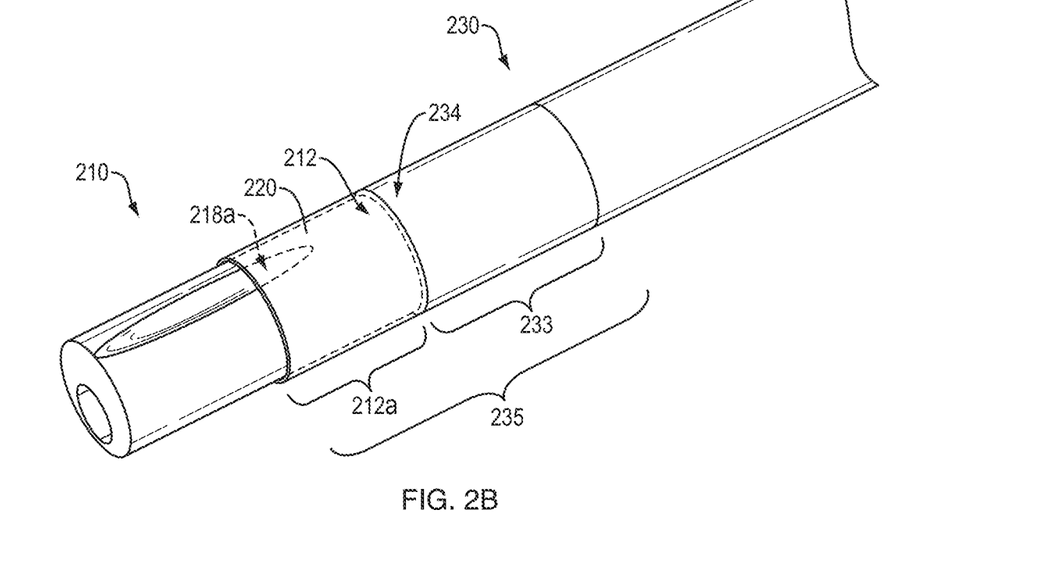

In one embodiment, an endcap of the present disclosure may be configured for attachment to a delivery device (e.g., catheter). Referring to FIG. 2A, a delivery device 230 may include a distal portion 233 which defines a recessed portion 233a (e.g., pocket) configured to receive the endcap 210. The outer surface 220 of the endcap 210 may form an interference or friction fit within the recessed portion 233a sufficient to prevent the endcap from dislodging during use (e.g., within the patient). In addition, or alternatively, the endcap 210 may be secured within the recessed portion 233a by a suitable weld, solder, braze, adhesive, glue and/or resin. The recessed portion 233a may further include a skived opening 233b configured to align with the second opening 218a of the endcap 210. Referring to FIG. 2B, the proximal end 212 of the endcap 210 may be attached to the distal end 234 of the delivery device 230 by a sleeve 235 disposed about an outer surface 220 of the endcap 210 proximal portion 212a and an outer surface of the delivery device 230 distal portion 233. The sleeve 235 may cover a limited portion of the second opening 218a. In one embodiment, the sleeve 235 may include a heat shrink material configured to secure the endcap 210 to the delivery device 230 without substantially increasing the thickness of the delivery device or endcap. In addition, or alternatively, the sleeve 235 may be secured to the delivery device and endcap by an interference fit and/or a suitable weld, solder, braze, adhesive, glue or resin.

Figure 3A:
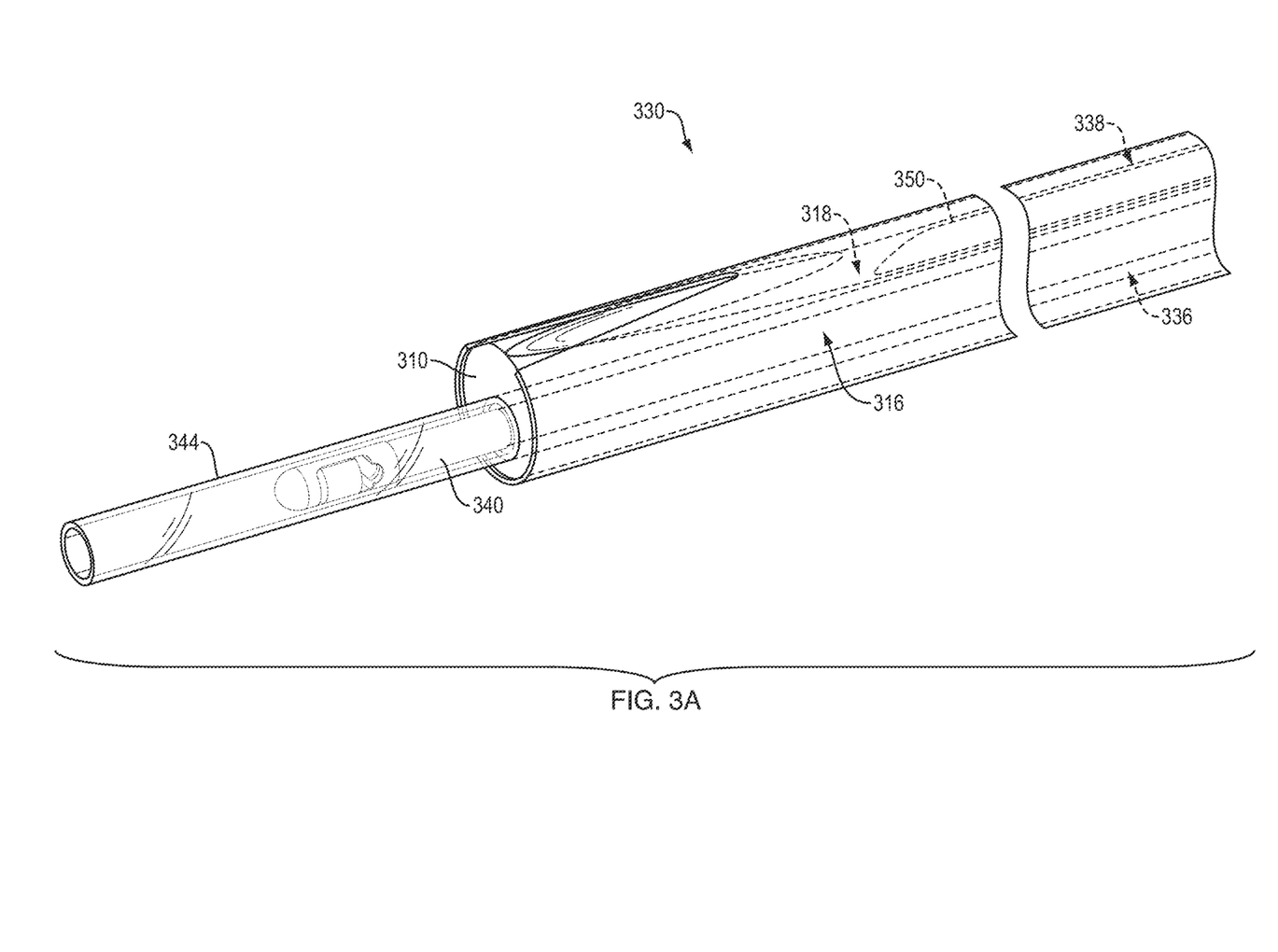
FIGS. 3A-3B provide schematic views of a tissue sampling system, according to one embodiment of the present disclosure.
Figure 3B:
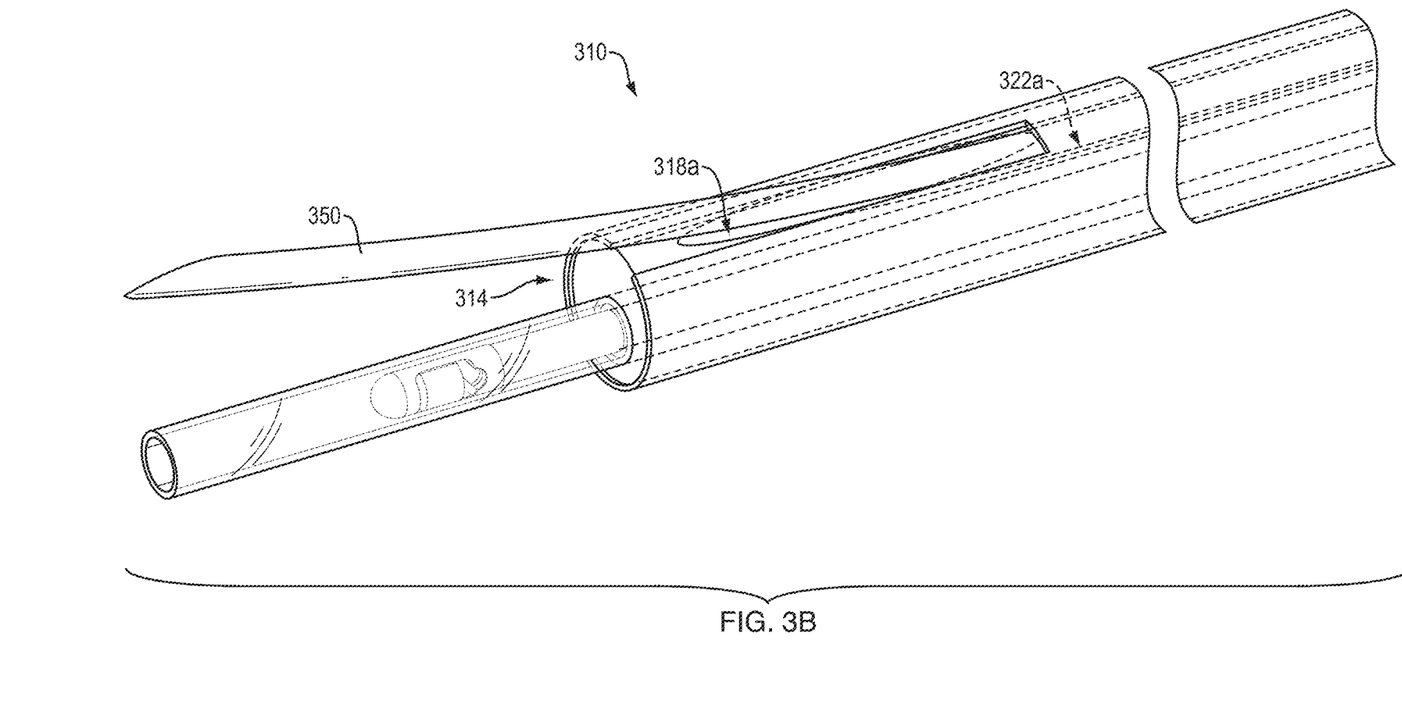

Referring to FIG. 3A, the delivery device 330 may include first and second working channels 336, 338 such that when the endcap 310 is secured to the delivery device, the first working channel 336 aligns with and forms a contiguous lumen with the first lumen 316, and the second working channel 338 aligns with and forms a contiguous lumen with the second lumen 318. The contiguous first working channel 336 and first lumen 316 may be configured to receive an ultrasound transducer 340 disposed within a flexible sheath 344. The sheath 344 may extend distally beyond the ultrasound transducer 340 to protect the ultrasound transducer as the delivery device 330 is advanced through a body passage. The sheath 344 may also provide a conduit through which a medical professional may intermittently introduce a suitable fluid (e.g., isotonic saline, etc.) for consistent and reliable propagation of ultrasound energy. In one embodiment, the sheath 344 and ultrasound transducer 340 may be fixedly disposed within the contiguous first working channel 336 and first lumen 316. In another embodiment, the sheath 344 and ultrasound transducer 340 may be slidably disposed within the contiguous first working channel 336 and first lumen 316. In yet another embodiment, the ultrasound transducer may include a radial ultrasound probe which is rotatably disposed within the sheath 344. The contiguous second working channel 338 and second lumen 318 may be configured to slidably receive a tissue sampling element 350 (e.g., biopsy needle). Referring to FIG. 3B, the tissue sampling element 350 may be distally advanced along ramped surface 322a of the endcap 310 such that the tissue sampling element 350 deflects (e.g., bends) away from a longitudinal axis of the endcap 310 upon exiting the second opening 318a. When the tissue sampling element 350 is actuated beyond the distal end 314 of the endcap 310, the tissue sampling element 350 and ultrasound transducer 340 are offset relative to each other by approximately 180 degrees. Stated differently, the tissue sampling element 350 exits the second opening 318a at a location on the endcap 310 that is directly opposite (e.g., directly above) the ultrasound transducer 340. Alternatively, the tissue sampling element and ultrasound transducer may be offset relative to each other by an angle that is less than 180 degree (e.g., approximately 90 degrees, approximately 100 degrees, approximately 110 degrees, approximately 120 degrees, approximately 130 degrees, approximately 140 degrees, approximately 150 degree, approximately 160 degrees, approximately 170 degrees), or by an angle that is greater than 180 degrees (e.g., approximately 190 degrees, approximately 200 degrees, approximately 210 degrees, approximately 220 degrees, approximately 230 degrees, approximately 240 degrees, approximately 250, approximately 260 degrees, approximately 270 degrees).

Figure 4A:
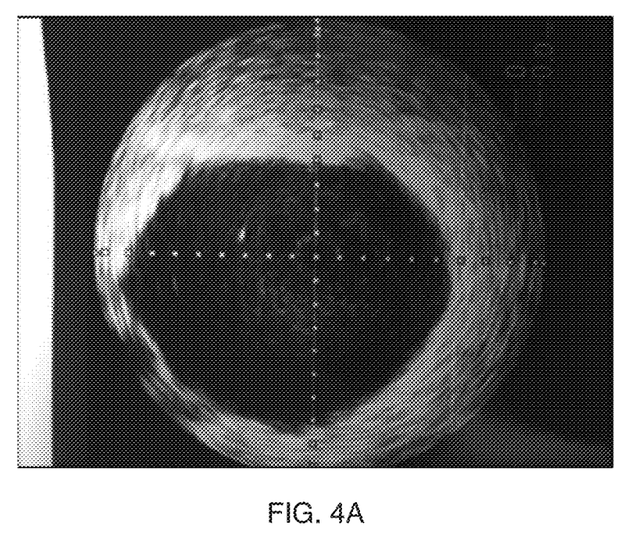
FIGS. 4A-4B provide representative ultrasound images of concentric (FIG. 4A) and eccentric (FIG. 4B) pulmonary nodules, according to one embodiment of the present disclosure.
Figure 4B:
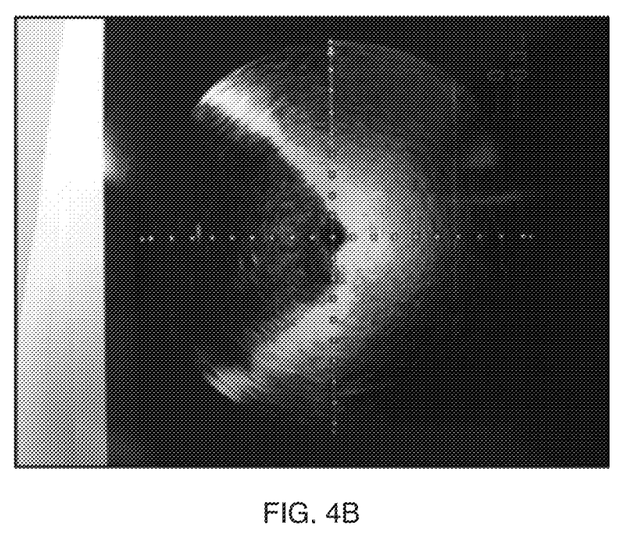

The ultrasound images of FIGS. 4A-4B demonstrate the morphological difference between a concentric pulmonary nodule (FIG. 4A) that occupies a central portion of the pulmonary passage, and an eccentric pulmonary nodule (FIG. 4B) that is disposed on a side portion of the pulmonary passage.

Figure 5A:
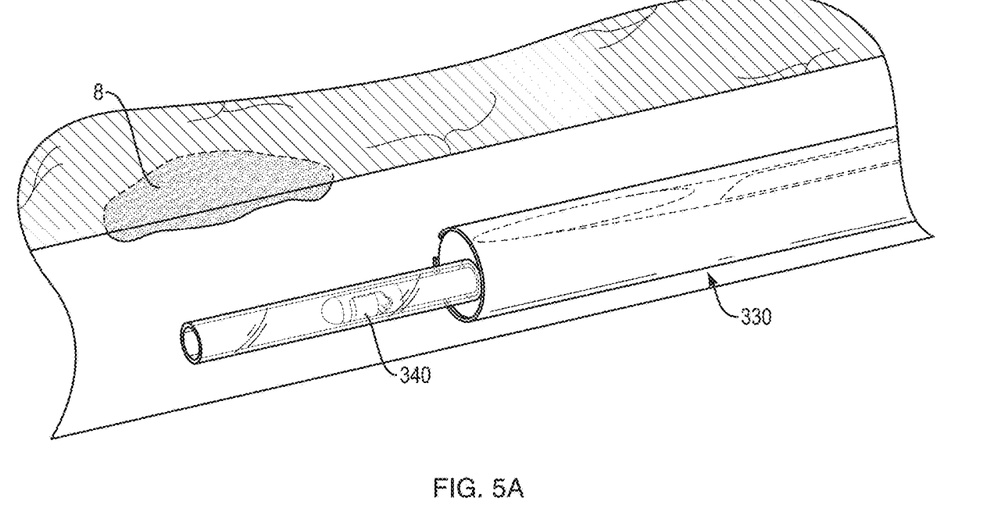
FIGS. 5A-5F illustrate the steps involved in sampling an eccentric pulmonary nodule, according to one embodiment of the present disclosure.
Figure 5B:
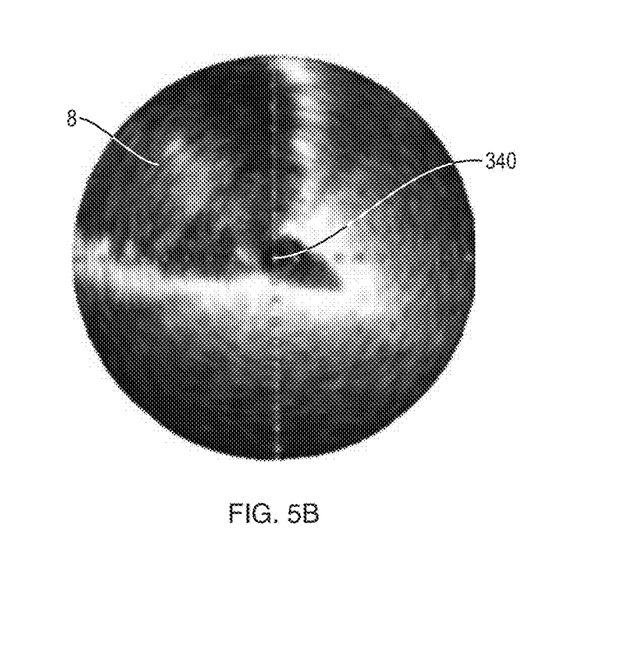
Figure 5C:
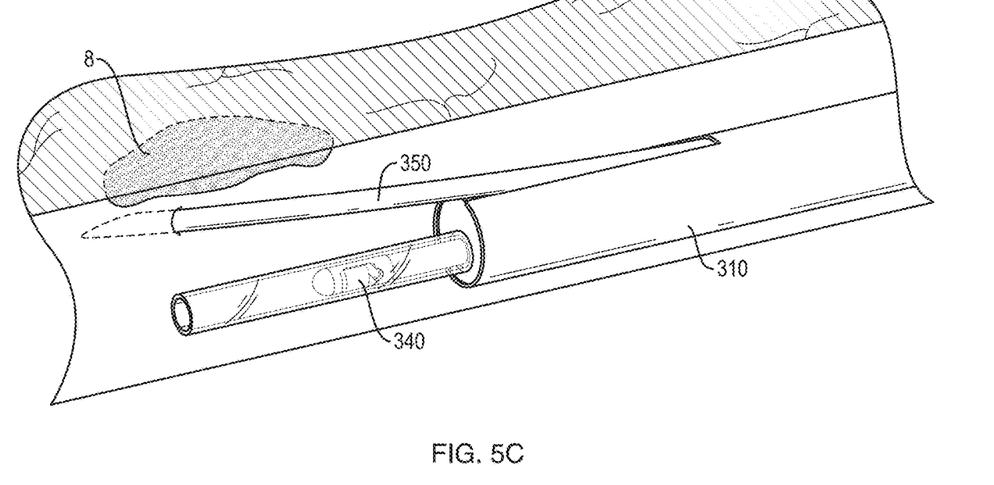
Figure 5D:
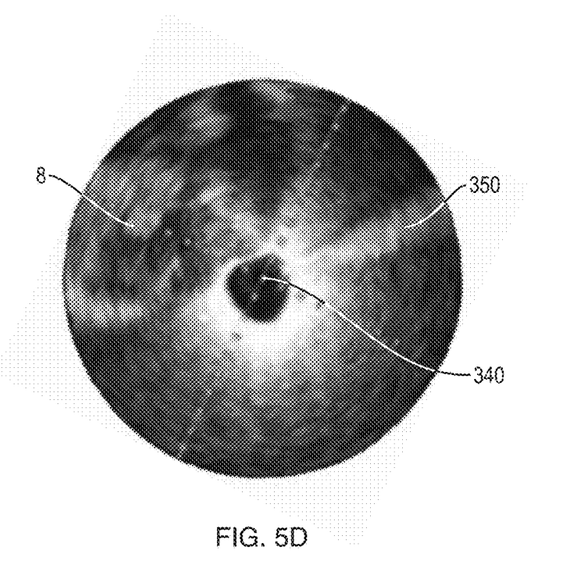
Figure 5E:
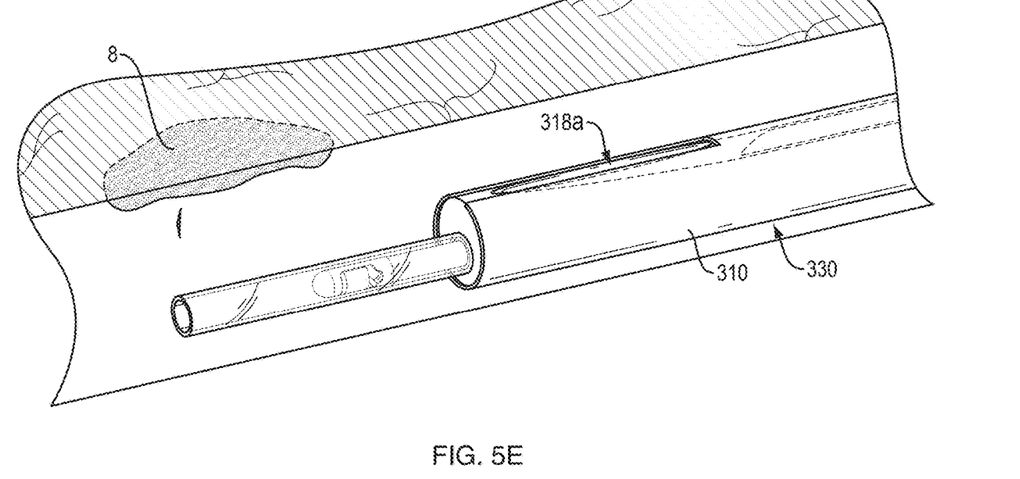
Figure 5F:
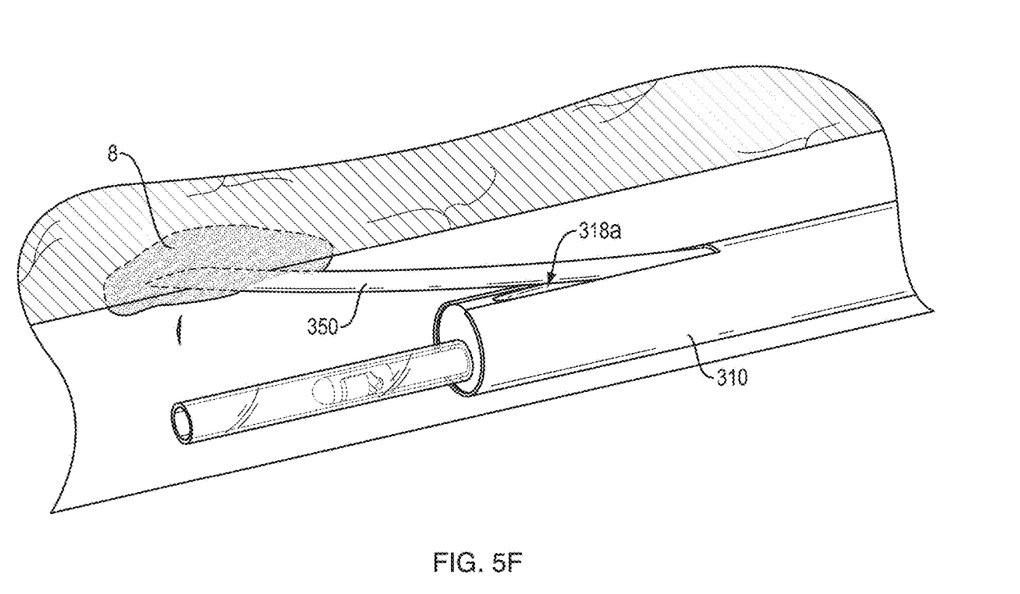

Referring to FIGS. 5A-5F, in use and by way of example, a bronchoscope (not depicted) may be advanced through the trachea and into a bronchial passage in the vicinity of a target tissue site (e.g., pulmonary nodule). The delivery device 330 (e.g., catheter) of FIG. 3A may be advanced through and distally beyond a working channel of the bronchoscope to provide an ultrasound image of the bronchial passage. As the delivery device approaches the target tissue site, the ultrasound transducer 340 may provide an ultrasound image of the eccentric nodule 8 (FIG. 5A). As illustrated in FIG. 5B, the eccentric nodule 8 may appear as a dark lesion in the upper left quadrant of the ultrasound image, relative to ultrasound transducer 340 that is identifiable as a dark circle in the center of the ultrasound image. With the ultrasound transducer 340 positioned in the vicinity of the eccentric nodule 8, the medical professional may actuate (e.g., distally advance) the tissue sampling element 350 through the second opening 318a of the endcap 310 into the wall of the pulmonary passage (FIG. 5C). As illustrated in FIG. 5D, the tissue sampling element 350 first appears on the ultrasound image after being actuated (e.g., distally advanced) beyond the ultrasound transducer 340. In the event that the tissue sampling element 350 does not penetrate the eccentric nodule following the first actuation, the medical professional may retract the tissue sampling element 350 into the endcap 310, rotate the entire delivery device 330 based on the relative location of the tissue sampling element 350 and eccentric nodule 8 (FIGS. 5C-5D) to align the second opening 318a with the eccentric nodule 8 (FIG. 5E), and then re-actuate the tissue sampling element 350 through the second opening 318a of the endcap 310 into the eccentric nodule 8 (FIG. 5F). The tissue sampling element 350 may then be retracted into the endcap 310 and the delivery device 330 proximally retracted into the bronchoscope and removed from the patient. The biopsy sample of the eccentric nodule may then be removed from within the lumen of the tissue sampling element 350 for cytologic evaluation. Although the tissue sampling element 350 of FIG. 5C is shown as penetrating the wall of the bronchial passage at a location that does not enter the eccentric nodule 8 (e.g., the target nodule is "missed"), in various embodiments the tissue sampling element 350 may be actuated distally beyond the ultrasound transducer 340 such that the end (e.g., sharpened point) of the tissue sampling element 350 appears on the ultrasound image but does not extend into the wall of the bronchial passage. The medical professional may then rotate the entire delivery device 330 to align the exposed tissue sampling element 350 with the eccentric nodule 8, and then completely or fully actuate the tissue sampling element 350 into the eccentric nodule 8. While the delivery system of FIG. 3A may be advantageous over conventional needle aspiration systems, it may be beneficial for the medical professional to determine the location/orientation of a biopsy needle relative to the target pulmonary nodule while the biopsy needle is housed within the endcap and/or delivery device (e.g., prior to its first actuation).

Figure 6A:
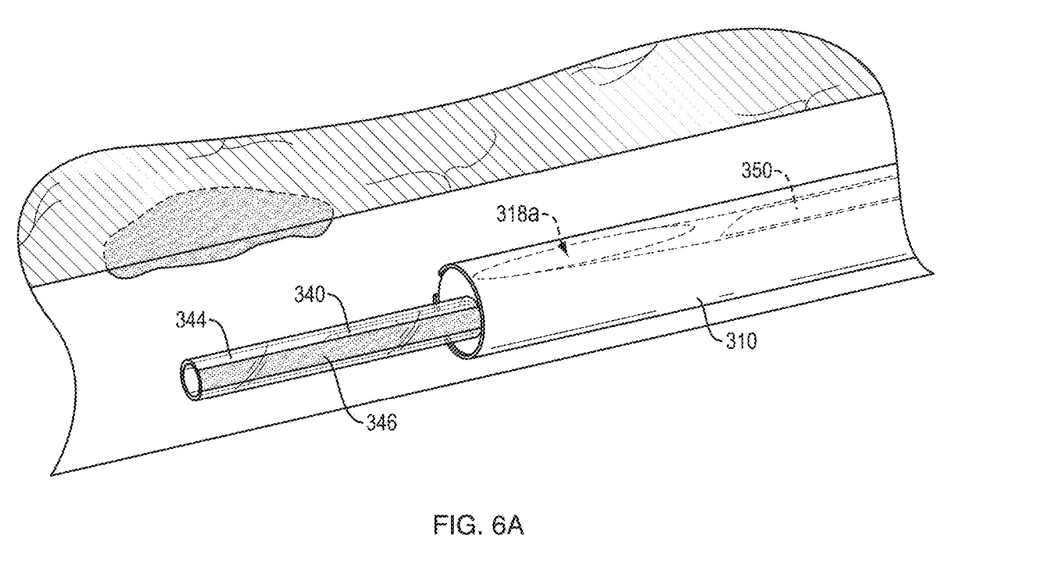
FIGS. 6A-6D illustrate the steps involved in sampling an eccentric pulmonary nodule, according to one embodiment of the present disclosure.
Figure 6B:
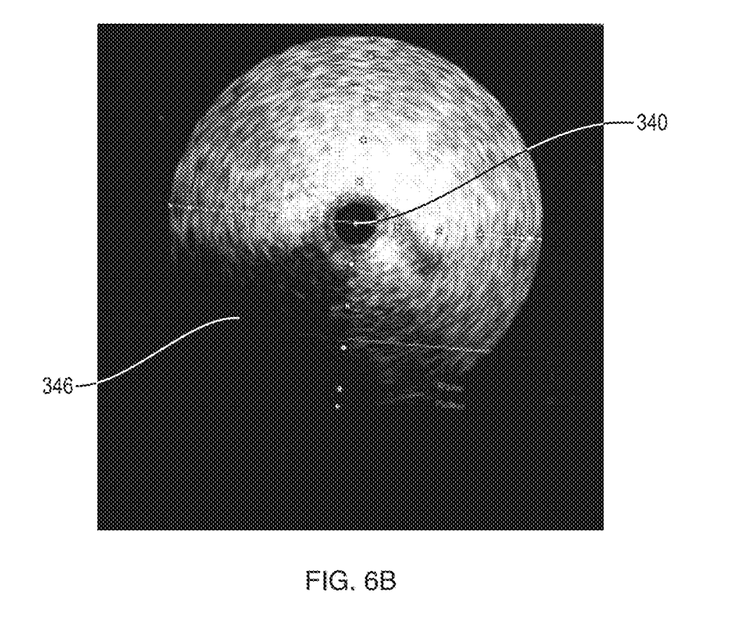

Referring to FIG. 6A, in one embodiment, the delivery device of FIG. 3A may include an ultrasound transducer 340 disposed within a flexible sheath 344 that further includes a radiopaque material disposed in a "strip" 346 along a length of a portion of the sheath. For example, the radiopaque material may be integrally formed within the sheath 344 during the extrusion process. Referring to FIG. 6B, the strip 346 of radiopaque material may provide a radiopaque marker which is visible as a dark portion (e.g., slice) on the ultrasound image. As discussed above, because the tissue sampling element 350 exits the second opening 318a of the endcap 310 and extends directly opposite (e.g., directly above) the ultrasound transducer 340, the fixed location of the sheath 344 and radiopaque strip 346 allows the medical professional to identify where the tissue sampling element 350 will appear prior to its actuation.

Figure 6C:
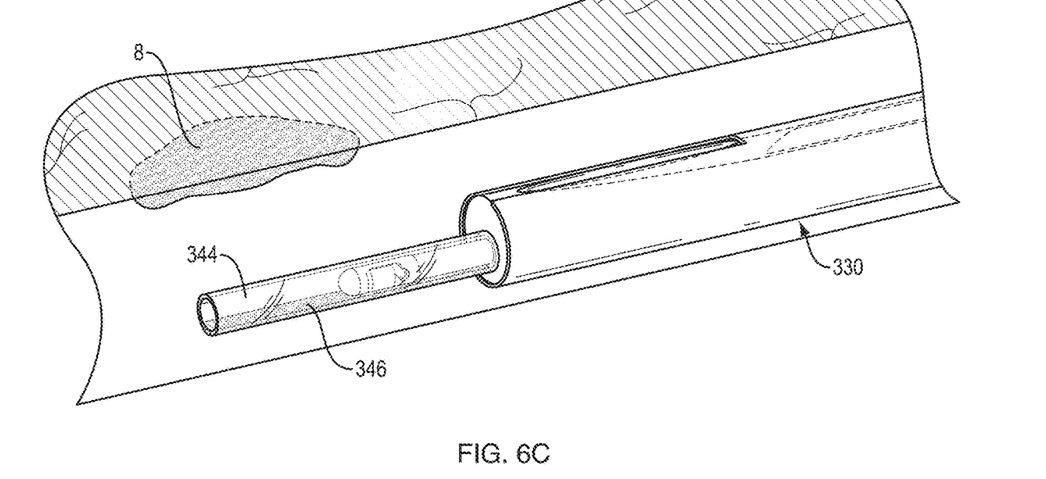
Figure 6D:
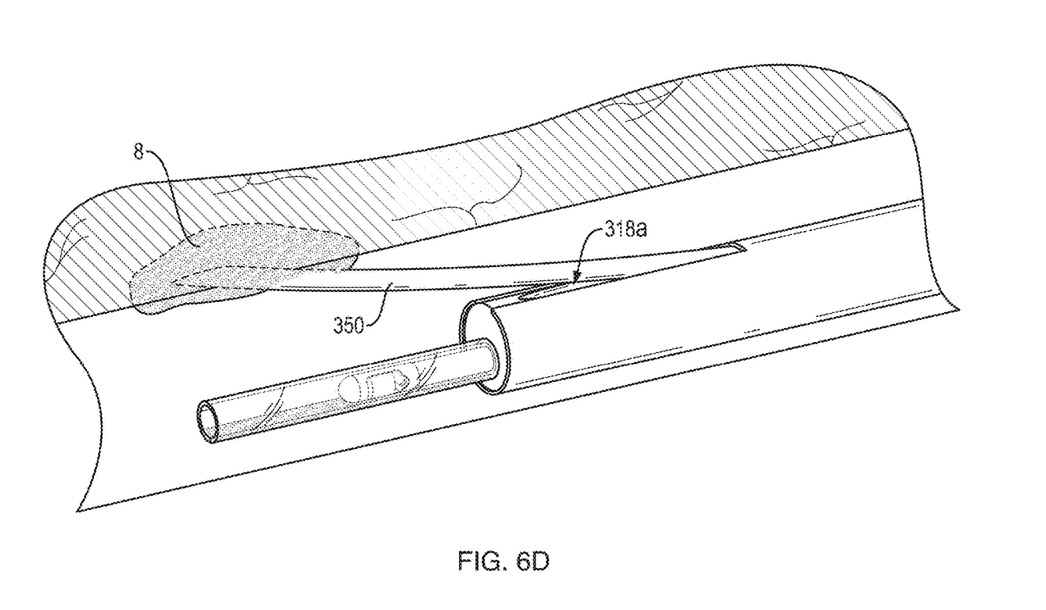

In use, and by way of example, a bronchoscope (not depicted) may be advanced through the trachea and into a bronchial passage in the vicinity of a target tissue site (e.g., pulmonary nodule). The delivery device 330 (e.g., catheter), including a sheath 344 and radiopaque strip 346, may be advanced through and distally beyond a working channel of the bronchoscope to provide an ultrasound image of the bronchial passage. As the delivery device approaches the target tissue site, the ultrasound transducer 340 may provide an ultrasound image of both the eccentric nodule 8 and the radiopaque strip 346 (FIGS. 6A-6B). The delivery device 330 may then be rotated such that the radiopaque strip 346 and eccentric nodule 8 appear on opposite sides of the ultrasound image (FIG. 6C). The tissue sampling element 350 may then be actuated through the second opening 318*a* of the endcap 310 into eccentric nodule 8 (FIG. 6D). The tissue sampling element 350 may be repeatedly retracted and actuated into the eccentric nodule depending on the amount of biopsy tissue needed, without concern about surrounding healthy tissue. The tissue sampling element 350 may then be retracted into the endcap 310 and the delivery device 330 proximally retracted into the bronchoscope and removed from the patient. The biopsy sample of the eccentric nodule may then be removed from within the lumen of the tissue sampling element 550 for cytologic evaluation.

The medical devices of the present disclosure are not limited to bronchoscopes, and may include a variety of medical devices for accessing body passageways, including, for example, catheters, ureteroscopes, duodenoscopes, colonoscopes, arthroscopes, cystoscopes, hysteroscopes, and the like.

Finally, although the embodiments of the present disclosure have been described in use with a bronchoscope, the delivery device of the present disclosure may be positioned within the patient in the absence of an accompanying medical device. For example, the medical device may be introduced into the patient through a working channel of the medical instrument itself.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An apparatus comprising:
   a dual lumen catheter;
   a tissue sampling element disposed in a first lumen of the dual lumen catheter, the tissue sampling element actuatable between an unactuated state and an actuated state;
   a radial ultrasound transducer disposed in a second lumen of the dual lumen catheter, the radial ultrasound transducer to image only one marker to generate a first radial image when the tissue sampling element is in the unactuated state and image the one marker and the tissue sampling element to generate a second radial image when the tissue sampling element is in the actuated state,
   wherein the one marker has a fixed position relative to the ultrasound transducer and the tissue sampling element when in the actuated state, and
   wherein a position of the marker in the first radial image indicates a position of the tissue sampling element in the second radial image; and
   an endcap attached to the second lumen of the dual lumen catheter comprising a proximal end and a distal end, wherein the tissue sampling element when in the actuated state is beyond the distal end of the endcap, the tissue sampling element and radial ultrasound transducer are offset relative to each other.

2. The apparatus of claim 1, wherein the marker comprises a radiopaque strip.

3. The apparatus of claim 1, comprising a delivery device including first and second lumens, the first lumen extending between a proximal end and a distal end of the delivery device and the second lumen extending between the proximal end and an outer surface of the delivery device, wherein the tissue sampling element is disposed within the first lumen of the delivery device and the ultrasound transducer is disposed within the second lumen of the delivery device.

4. The apparatus of claim 3, wherein the first lumen of the delivery device includes a ramped surface.

5. The apparatus of claim 4, wherein the ramped surface includes an angle of approximately 5 degrees to approximately 10 degrees relative to a longitudinal axis of the ultrasound transducer.

6. An apparatus comprising:
   A dual lumen catheter;
   a biopsy needle disposed in a first lumen of the dual lumen catheter, the biopsy needle actuatable between an unactuated state and an actuated state;
   a radial ultrasound transducer disposed in a second lumen of the dual lumen catheter, the radial ultrasound transducer to image only one marker to generate a first radial image when the biopsy needle is in the unactuated state and image the one marker and the biopsy needle to generate a second radial image when the biopsy needle is in the actuated state,
   wherein the one marker has a fixed position relative to the ultrasound transducer and the biopsy needle when in the actuated state, and
   wherein a position of the marker in the first radial image indicates a position of the biopsy needle in the second radial image; and
   an endcap attached to the second lumen of the dual lumen catheter comprising a proximal end and a distal end, wherein the biopsy needle when in the actuated state is beyond the distal end of the endcap, the biopsy needle and radial ultrasound transducer are offset relative to each other.

7. The apparatus of claim 6, wherein the marker comprises a radiopaque strip.

8. The apparatus of claim 6, comprising a delivery device including first and second lumens, the first lumen extending between a proximal end and a distal end of the delivery device and the second lumen extending between the proximal end and an outer surface of the delivery device, wherein the biopsy needle is disposed within the first lumen of the delivery device and the ultrasound transducer is disposed within the second lumen of the delivery device.

9. The apparatus of claim 8, wherein the first lumen of the delivery device includes a ramped surface.

10. The apparatus of claim 9, wherein the ramped surface includes an angle of approximately 5 degrees to approximately 10 degrees relative to a longitudinal axis of the ultrasound transducer.

\* \* \* \* \*